US011189378B2

(12) United States Patent
Singh et al.

(10) Patent No.: US 11,189,378 B2
(45) Date of Patent: Nov. 30, 2021

(54) AUTOMATED STERILIZATION SYSTEM WITH ARTIFICIAL INTELLIGENCE FOR PROCESSING SURGICAL INSTRUMENTS AND METHODS EMPLOYED THEREOF

(71) Applicants: Raj Singh, Markham (CA); Ushvinder Bhatia, Mississauga (CA)

(72) Inventors: Raj Singh, Markham (CA); Ushvinder Bhatia, Mississauga (CA)

(73) Assignees: Raj Singh, Markham (CA); Ushvinder Bhatia, Mississauga (CA)

( * ) Notice: Subject to any disclaimer, the term of this patent is extended or adjusted under 35 U.S.C. 154(b) by 188 days.

(21) Appl. No.: 16/528,651

(22) Filed: Aug. 1, 2019

(65) Prior Publication Data
US 2020/0043604 A1 Feb. 6, 2020

Related U.S. Application Data

(60) Provisional application No. 62/713,547, filed on Aug. 2, 2018.

(51) Int. Cl.
| | |
|---|---|
| *G06K 7/14* | (2006.01) |
| *G06K 19/06* | (2006.01) |
| *G06K 7/10* | (2006.01) |
| *G16H 40/40* | (2018.01) |
| *G06N 5/02* | (2006.01) |

(Continued)

(52) U.S. Cl.
CPC ............. *G16H 40/40* (2018.01); *A61B 90/96* (2016.02); *A61B 90/98* (2016.02); *A61L 2/24* (2013.01); *G06K 7/10366* (2013.01); *G06K 7/1413* (2013.01); *G06K 19/06028* (2013.01); *G06N 5/02* (2013.01); *A61L 2202/14* (2013.01)

(58) Field of Classification Search
CPC .. A61L 2/00; A06L 9/00; G05B 15/00; G06Q 10/08; G06Q 10/087
USPC .......................... 422/3, 1; 235/375, 487, 470
See application file for complete search history.

(56) References Cited

U.S. PATENT DOCUMENTS

| | | | |
|---|---|---|---|
| 10,944,728 B2* | 3/2021 | Wiener | G16H 80/00 |
| 2007/0001839 A1* | 1/2007 | Cambre | G06Q 10/08 |
| | | | 340/539.12 |

(Continued)

*Primary Examiner* — Edwyn Labaze

(57) ABSTRACT

Exemplary embodiments of the present disclosure are directed towards an artificial intelligence sterilization system and a novel process of providing outsourced sterilization services for processing surgical instruments comprising of: a GUI module along with wizards representing an interactive user interactions to direct to the next action to be performed, authentication module comprising of RFID authentication/AI facilitated control of protective gear worn by the users as well as the workspace, sterilizer's module configured to automate, control and track sterilizer level operations; cassettes module configured to automate, control and track surgical lab instruments with RFID or AI tracking and place instruments in their respective cassettes; patient's module configured to deal with the surgical lab instruments to cassettes to equipment to patient tracking; audit and reporting module configured to deal with a detailed audit report; training module providing context based training modules and reference manuals, inventory module providing requirement based auto replenishments of the surgical lab instruments directed by artificial intelligence.

17 Claims, 15 Drawing Sheets

(51) Int. Cl.
 *A61B 90/96* (2016.01)
 *A61B 90/98* (2016.01)
 *A61L 2/24* (2006.01)

(56) References Cited

U.S. PATENT DOCUMENTS

| | | | |
|---|---|---|---|
| 2011/0005342 A1* | 1/2011 | Treat | A61L 2/22 |
| | | | 73/865.8 |
| 2013/0108503 A1* | 5/2013 | Ramkhelawan | A61B 50/20 |
| | | | 422/1 |
| 2014/0083886 A1* | 3/2014 | Winterrowd | A61B 50/34 |
| | | | 206/370 |
| 2014/0125482 A1* | 5/2014 | Rigsby | A61B 17/7001 |
| | | | 340/539.13 |
| 2018/0105787 A1* | 4/2018 | Hardin | C12M 41/34 |
| 2019/0255207 A1* | 8/2019 | Oko | A61L 2/26 |
| 2020/0030476 A1* | 1/2020 | Corsini | A61L 2/24 |
| 2021/0236676 A1* | 8/2021 | Araujo Dalla Bona | A61L 2/06 |

* cited by examiner

AUTOMATED STERILIZATION SYSTEM WITH ARTIFICIAL INTELLIGENCE FOR PROCESSING SURGICAL INSTRUMENTS AND METHODS EMPLOYED THEREOF

CROSS-REFERENCE TO RELATED APPLICATIONS

This patent application claims priority benefit of U.S. Provisional Patent Application No. 62/713,547, entitled "Automated Sterilization System with Artificial Intelligence for Processing Surgical Instruments and Methods Employed Thereof", filed on 2 Aug. 2018. The entire contents of the patent application are hereby incorporated by reference herein in its entirety.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

TECHNICAL FIELD

The present disclosure generally relates to the field of automated sterilization processes. More particularly, the present disclosure relates to an artificial intelligence system for automating, controlling and tracking the sterilization process for instruments (surgical, dental or others) and methods employed thereof.

BACKGROUND

Sterilization compromise induced threat to life cases have reportedly increased significantly across the world. The hospital and other authorities handling the sterilization of surgical instruments are blamed for growing non-compliance to prescribed standards. They have been using archaic instrument handling systems that do not provide validation and accountability and leave a lot of room for errors and omissions, thereby putting the patient at risk for compromised healthcare and the practitioners at risk of liability.

The rules and regulations governing Instrument Reprocessing has recently become a source of huge concern and stress to practitioners and staff members in the dental and medical fields. This is due to a number of factors:

Practices have been subjected to random inspections and in a number of cases have been closed for varying periods of time, thereby having disastrous effects on the practice, as patients are informed and tend to leave the practice in mass.

The guidelines from public health and the governing bodies of the medical doctors and dentists differ and there is much confusion regarding the exact processes needed to satisfy everyone.

In addition, they are constantly evolving and changing as the various agencies rush to attempt to update their recommendations, and requirements in light of the above.

The guidelines and requirements from the various agencies also vary from practice to practice as they are dependent on the procedures performed in that particular practice. Even within a practice, the requirements for reprocessing instruments vary based on the type of procedure being performed with those instruments.

Cleaning, disinfections & sterilization guidelines for healthcare facilities (hospitals, doctors, dentists, others) are convoluted, vary with geography, practitioner, equipment, and are constantly evolving. The current sterilization operations in various healthcare facilities are totally manually-controlled, tracked and logged manually. It requires continuous staff training and is prone to high degree of human error. Audit requirements are extensive—requiring Manual logs, physical indicators, sterilizer report print outs. A number of practitioners have been shut down by the Government auditors.

BRIEF SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Exemplary embodiments of the present disclosure are directed towards an automated sterilization system with artificial intelligence for processing surgical instruments and methods employed thereof.

An exemplary object of the present disclosure is directed towards automation of end to end sterilization process using artificial intelligence; rules based workflows, and wizards.

Another exemplary object of the present disclosure is directed towards the unique style of GUI which a pictorial view is laid out similar to the practitioner's physical work area. GUI incorporates control/guidance using wizards and workflows.

Another exemplary object of the present disclosure is directed towards novel way of user authentication using RFID and AI Scans.

Another exemplary object of the present disclosure is directed towards automated determination of physical indicators pass/fail status using AI photo recognition scans.

Another exemplary object of the present disclosure is directed towards an intelligent barcoding module.

Another exemplary object the present disclosure is directed towards validation and checks throughout the process of sterilization.

Another exemplary object the present disclosure is directed towards easy availability of cloud.

Another exemplary object the present disclosure is directed towards updated snapshots on indicators and reports on the cloud which is accessible as per the user's requirement.

Another exemplary object the present disclosure is directed towards a cost effective system compared to in house operations.

Another exemplary object the present disclosure is directed towards an efficient, time line proof record keeping mechanism.

Another exemplary object the present disclosure is directed towards reduction in consumption of human resources and real estate space.

Another exemplary object the present disclosure is directed towards availability of IPAC reports and automatically mailed to the physician or Office Manager daily if desired.

Another exemplary object the present disclosure is directed towards prevention and duplication of sterilization steps.

Another exemplary object the present disclosure is directed towards necessary steps that are enforced by the software to avoid staff errors and omissions.

Another exemplary object of the present subject matter is directed towards a novel process of providing outsourced sterilization services.

Yet another exemplary object of the present disclosure is directed towards automated services to facility and to the patient.

Another exemplary object of the present subject matter is directed towards a sterilizer's module configured to automate tests related to sterilizers with Bowie click (BD) barcoded, Biological Indicator (BI) barcoded based sterilizers test run using AI engines and AI photo recognition; a cassettes module configured to automate workflow, wizards and control of cassettes and equipment sterilization process using RFID or AI tracking a plurality of surgical lab instruments to their respective cassettes leveraging AI engines and AI photo recognition; a patient's module configured to link usage of cassettes and equipment to the patients providing end to end reporting with sterilizers to cassettes to equipment to patient tracking; an audit and reporting module configured to deal with a detailed end to end audit report from Sterilizers, cassettes to equipment to the patient level; a training module to deals with context based training modules and reference manuals, an inventory module to deals with requirement based auto replenishments of a plurality of surgical lab instruments using an artificial intelligence engine, and an outsourced module involving the tracking of inventory from practitioner, along with forward and reverse logistics.

According to an exemplary aspect, the automated sterilization system comprising an intelligent barcoding module configured to assign and read barcodes associated to a plurality of surgical lab instruments.

According to another exemplary aspect, the automated sterilization system further comprising an artificial intelligence engine configured to communicatively couple with the intelligent barcoding module for identifying the plurality of surgical lab instruments assigned with barcodes.

According to another exemplary aspect, the plurality of surgical lab instruments comprising at least one of: a sterilizer's module configured to automate, track and control sterilizer level test to ensure the plurality of surgical lab instruments are functioning as required; a cassettes module configured to automate, track and control cassettes/pouches end to end sterilization workflow in coordination with the guidance provided by the artificial intelligence engine.

According to another exemplary aspect, the automated sterilization system further comprising a database comprises essentials for the artificial intelligence engine to perform actions using each module, communications between each of the modules and the users which are captured in the database, the artificial intelligence engine configured to record a plurality of indicators of the plurality of surgical lab instruments.

According to another exemplary aspect, the automated sterilization system also comprising a graphic user interface (GUI) module communicatively connected to an authentication module.

According to another exemplary aspect, the authentication module enables to authenticate a plurality of user credentials and detection of User RFID tags and/or bracelets to authenticate and record user id as per the activity of the plurality of users and the graphic user interface module (GUI) module configured to represent a plurality of interactive user interactions for enabling a plurality of users to artificially relate to as a physical work space with a plurality of wizards to direct the plurality of users to login and perform an action.

BRIEF DESCRIPTION OF DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein:

FIG. 1 depicts a schematic representation of an environment for processing a plurality of surgical lab instruments requiring sterilization, according to one or more exemplary embodiments of the present disclosure.

DETAILED DESCRIPTION

Figure 1:
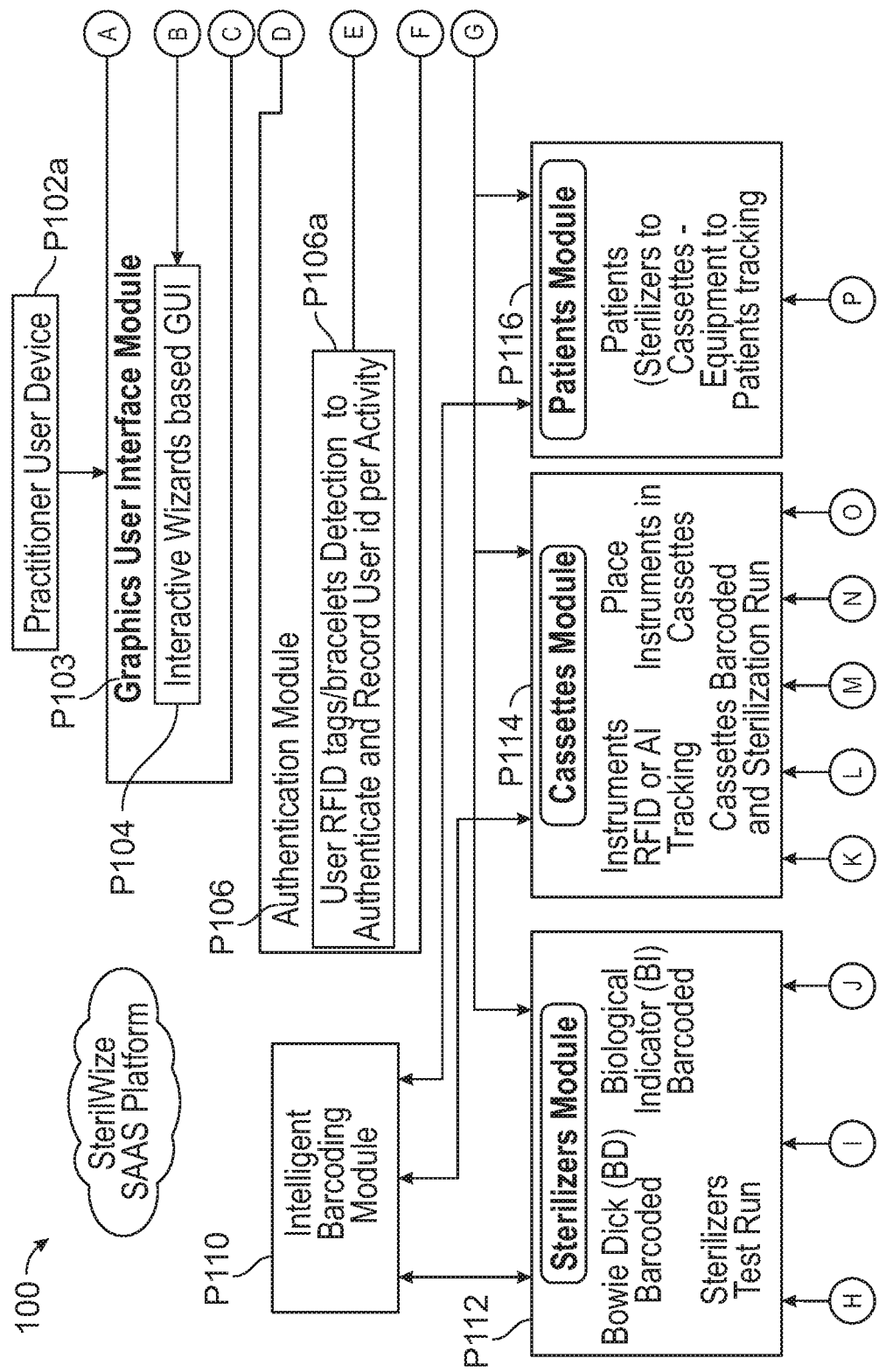
FIG. 1 is a block diagram representing an example environment in which aspects of the present disclosure can be implemented. Specifically.
Figure 1:
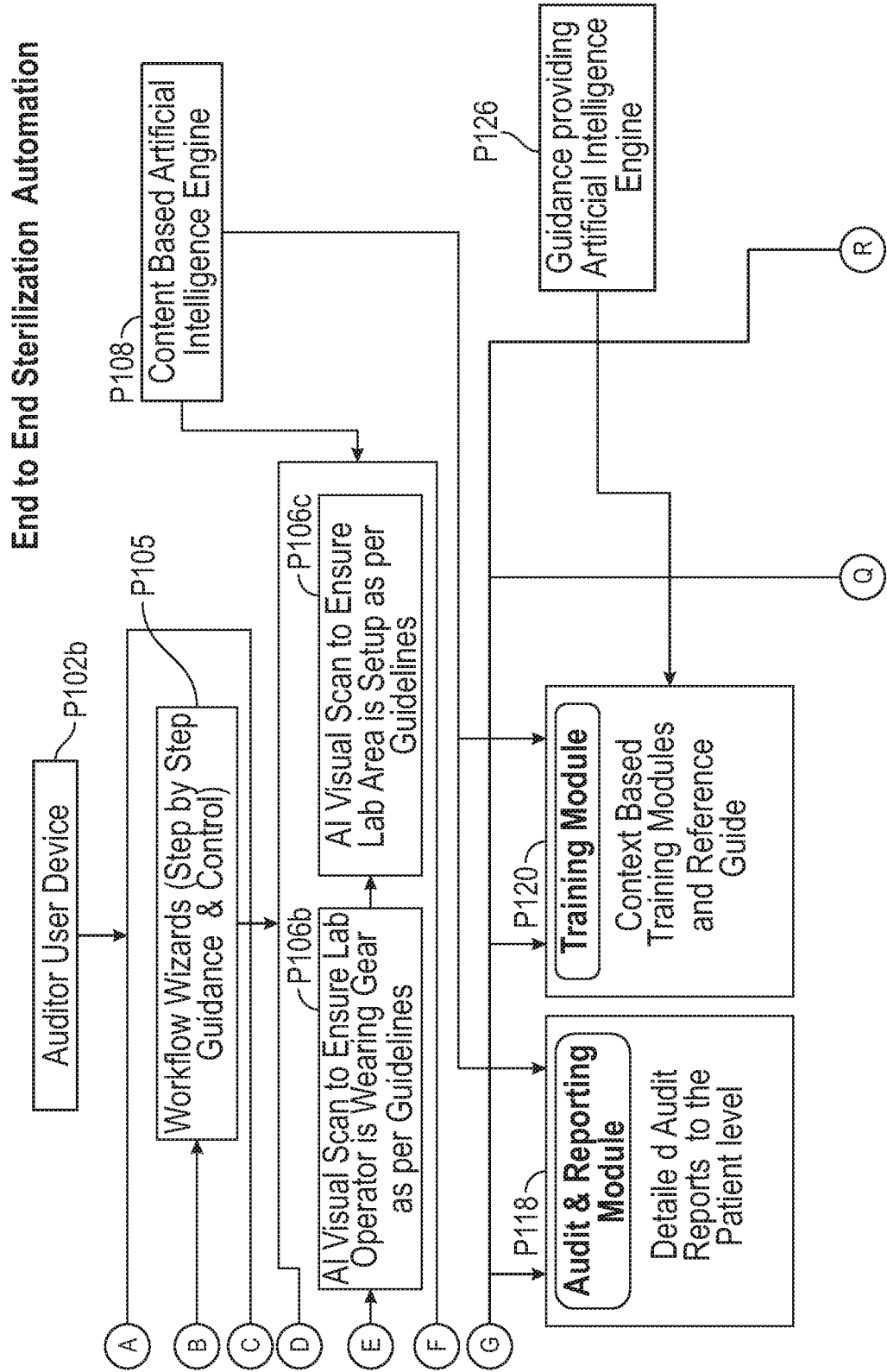
Figure 1:
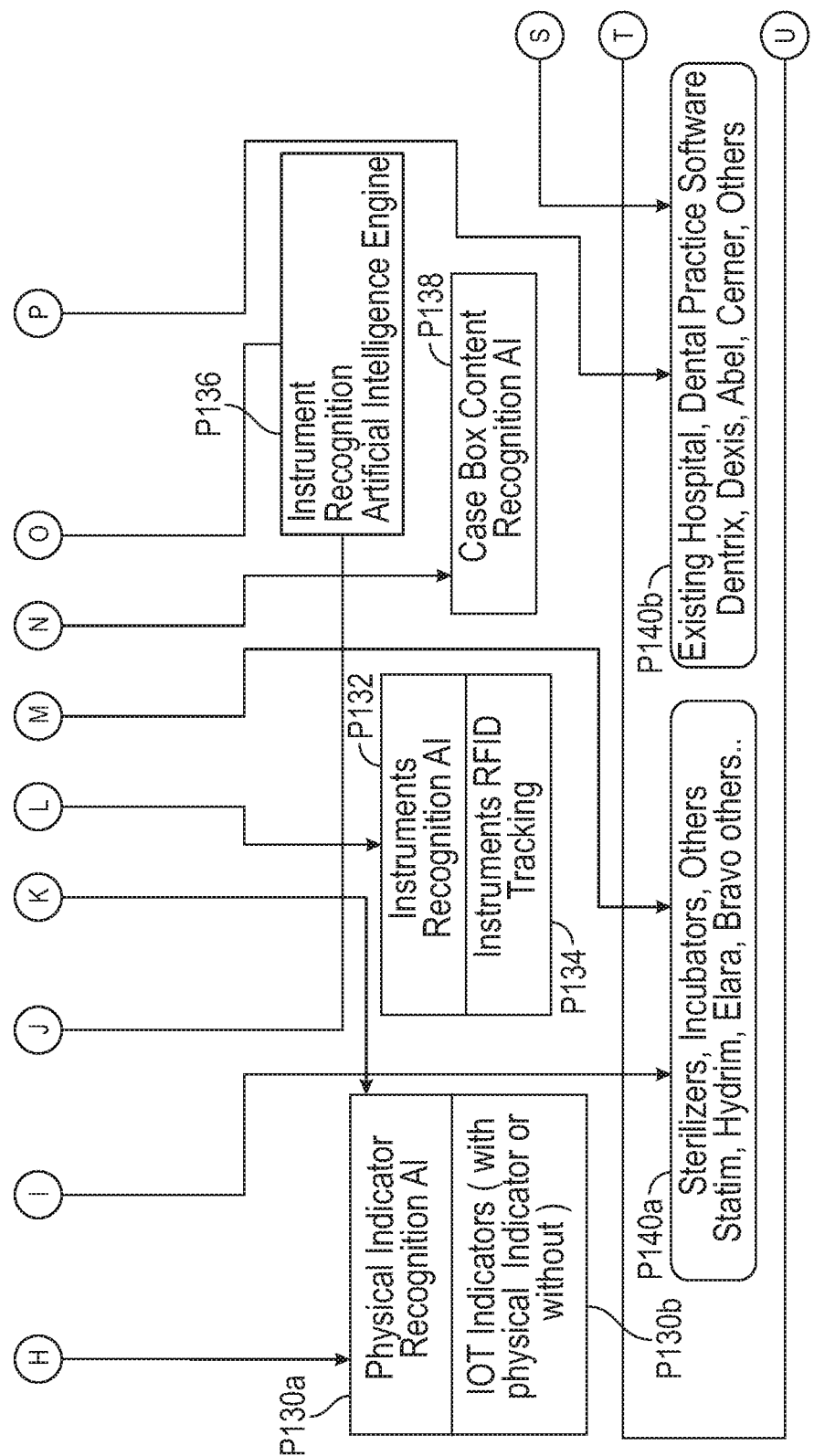
Figure 1:
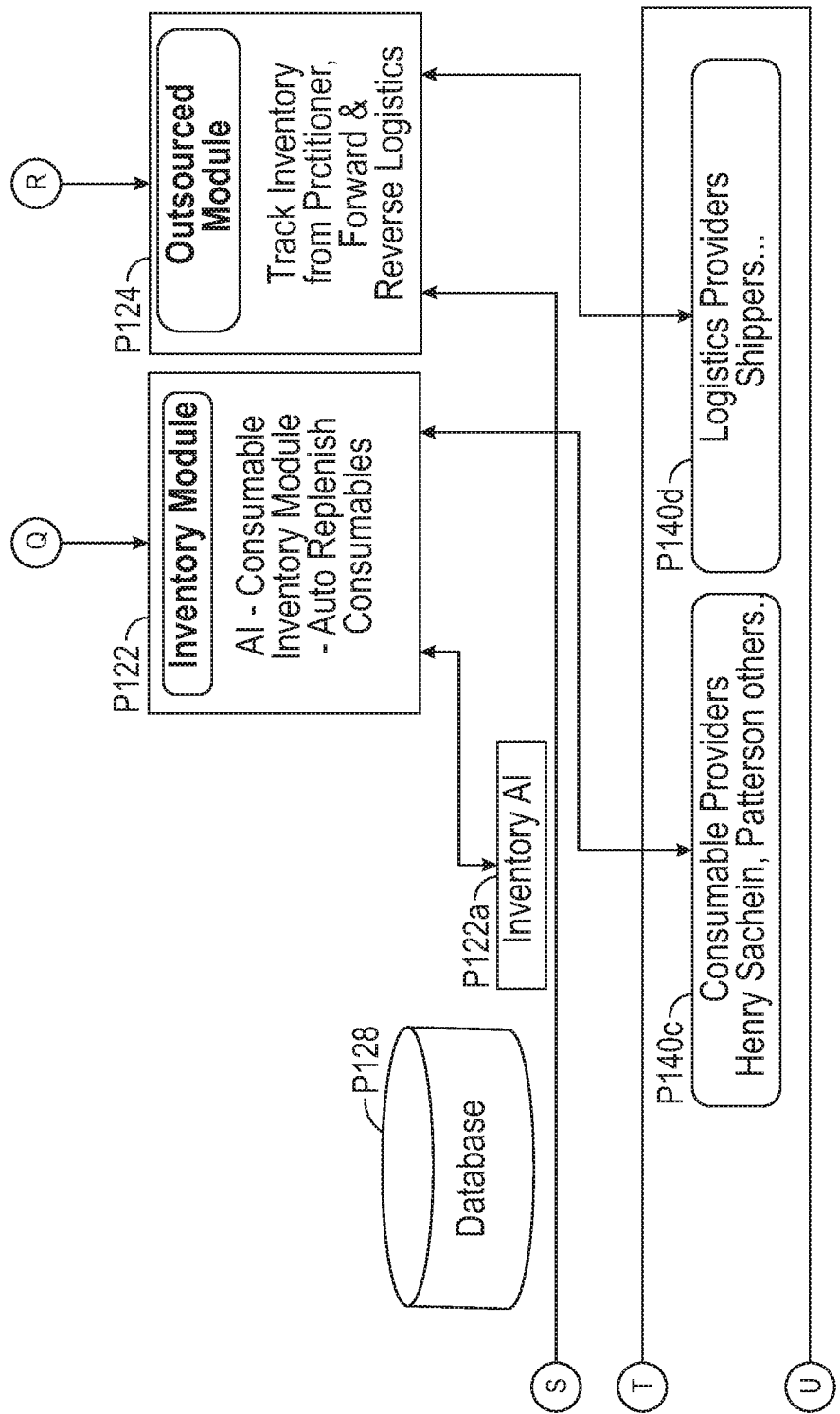

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

According to a non-limiting exemplary embodiment of the present disclosure, FIG. 1 is a block diagram 100, representing an example environment in which aspects of the present disclosure can be implemented. Specifically, FIG. 1 depicts a schematic representation of an environment for processing a plurality of surgical lab instruments requiring sterilization. The plurality of surgical lab instruments may comprise surgical, dental or other hospital related instruments. The term "User" relates to a practitioner, an auditor or a patient. FIG. 1 includes two users i.e. a practitioner and an auditor. The practitioner may be a physician, a dentist, a hospital staff, a paramedic, sterilization lab operator and the like. The auditors are representatives of the respective governments or other regulatory bodies who are bestowed with the task of conducting an audit of the sterilization process. Sterilization may be defined as a process incorporated for eliminating microorganisms in accordance with the prescribed standards. The practitioner and the user log into a cloud computing platform SAAS of the system, through their devices (P102a) and (P102b) respectively. These devices (P102a and P102b) include a display, not be limited to, a cathode ray tube (CRT), a liquid crystal display (LCD), a light-emitting diode (LED), a plasma, a smart phone, a tablet personal computer ("PC"), a mobile phone, a video telephone, an electronic book (e-book) reader, a desktop PC, a laptop PC, a netbook computer, a personal digital assistant ("PDA"), and the like. A graphics user interface module (GUI) (P103) comprises of interactive wizards based GUI (P104) and workflow wizards (P105). The workflow wizards (P105) are configured to perform as a set up assistant to define the workflow to the end user as a step by step process. For example: a flashing of the button may guide the user for the next step for the activity to be performed, not limiting to, click user manual, click add load, and the like. By logging in to the GUI module (P105) the users get to see the sterilization lab in front of them (on their respective devices) in real time. The authentication module (P106) enables to authenticate the credentials and compliance of the services with the prescribed standards. The step (P106a) involves the detection of User RFID tags and/or bracelets to authenticate and record user id as per the activity of the user. Instead of using an ID or password each user will have their custom RFID tag which will be used as a custom identity forsteps, not limiting to, loading of equipment, and the like. RFID code of the user will be logged with each activity performed by the user. The step (P106a) is the preliminary step towards sterilization. An AI visual Scan is performed (P106b) to ensure the sterilization lab Operator is wearing the gear as per guidelines prescribed by the best practices artificial intelligence (AI) engine (P108) using criteria applicable for the practitioner based on Geography, practice type etc. Similarly an AI visual scan (P106c) is done to ensure lab area is setup as per guidelines as per the best practices artificial intelligence engine (P108) using criteria applicable for the practitioner based on Geography, practice type etc. The wizards are configured to be based on artificial intelligence (P108) which is an intelligent rules engine. The activity inside the system takes place in various sub scenarios which are described in the form of modules. The artificial intelligence engine (P108) persistently updates itself based on, not limited to, best practices enforcement, online training, emergency procedures & workflows, and online manual. GUI module (P103) is connected to an authentication module (P106) which is connected to a sterilizer's module (P112), a cassettes module (P114), a patient's module (P116), an auditing and reporting module (P118), a training module (P120), an inventory module (P122), and an outsourced module (P124) in coordination with the artificial intelligence engine (P108), guidance providing artificial intelligence engine (P126), and an intelligent barcoding module (P110) wherever applicable. The sterilizer's module (P112) is configured to automate, track and control sterilizer level test to ensure sterilizers are functioning as required using various physical indicator test such as Bowie click (BD) tests, Biological Indicator (BI) tests in coordination with the guidance provided by the AI engine (P136), the cassettes module (P114) is configured to automate, track and control cassettes/pouches end to end sterilization workflow in coordination with the guidance provided by the instrument recognition artificial intelligence engine (P136). Instruments in cassettes/pouches are also tracked using RFID as well as AI photo scans. The patient's module (P116) is configured to automate control and track cassettes/equipment being applied to patients—this enables and end to end tracking with sterilizers to cassettes to equipment to patient tracking, audit and reporting module (P118) deals with detailed audit reports from Sterilizers, cassettes, equipment to the patient level, the training module (P120) deals with context based training modules and reference manuals, the inventory module (P122) deals with requirement based auto replenishments of the plurality of surgical lab instruments, and the outsourced module (P124) involves the tracking inventory from practitioner, along with forward and reverse logistics. The modules (P112 to P124) will be further discussed in detail in subsequent figures.

The database (depicted as sterilwize database) (P128) may include the essentials for the artificial intelligence engine (P108) to perform actions using each module. The interactions between each of the modules and the users and the end users are captured in the database (P128). The external interfaces here are not limited to, (P140a) sterilizer, incubators, others, Statim, Hydrim, Elara, Bravo others and (P140b) existing healthcare facilities like, hospitals, dental practice software Dentrix, Dexis, Abel, Cerner, and others, consumable providers henry sachein, Patterson others (P140c), and logistic providers and/or shippers (P140d). The physical indicator recognition AI (P130a) is configured to record the physical indicators and biological indicators of the surgical instruments (instruments from now on) intended to be put in the sterilizer (which will be depicted in FIG. 9) physical indicators are not limiting to, temperature, pressure, or time required for the cycle to be operated in order for the instruments to be sterilized. The sterilizers, cassettes/pouches, instruments and physical indicators are barcoded, not limiting to, Bowie Dick and/or Biological Indicator bar coded, where the biological indicators may not be limited to, bacterial spores and/or spore testing and the like. Similarly, the Internet of things (IOT) indicator (P130b) indicates whether the indicators have reached the optimal limit intended for sterilization. (P130b) is configured to work in collaboration with (P130a) or independently. The instruments recognition AI (P132) is configured to recognize the type of plurality of surgical lab instrument which not limiting to, forceps, tongs, clamps, curettes, dental instruments, and the like. Post recognition of the instrument comes into picture the cassettes module (P114), where the instruments RFID tracker (P134) decides as to which instrument would be going to which particular cassette which in turn would be loaded into the sterilizer. Both Instruments Recognition AI (P132) and the instruments RFID tracker (P134) interact with the cassettes module (P114). The inventory AI (P122a) is configured to continuously update the inventory of the number of consumables utilised. The artificial intelligence engine (P136) caters to, not limiting to, geographical, practitioner, equipment, and other guidelines. The AI Rules Engine (P136) continuously updates itself based on the evolving government guidelines which make it an intelligent self-learning engine. Case box recognition AI (P138) is the engine behind the cassettes module's (P114) feature for recognition of the case boxes.

In an embodiment, an automated sterilization system with artificial intelligence (AI) for processing surgical instruments, comprising: an intelligent barcoding module (P110) configured to assign and read barcodes associated to a plurality of surgical lab instruments. The artificial intelligence engine is configured to communicatively couple with the intelligent barcoding module (P110) for identifying the plurality of surgical lab instruments assigned with barcodes. The plurality of surgical lab instruments comprises at least one of: the sterilizer's module (P112) configured to automate, track and control sterilizer level test to ensure the plurality of surgical lab instruments are functioning as required; the cassettes module (P114) configured to automate, track and control cassettes/pouches end to end sterilization workflow in coordination with the guidance provided by the artificial intelligence engine. The database (P128) comprises essentials for the artificial intelligence engine to perform actions using each module, communications between each of the modules and the users which are captured in the database (P128). The artificial intelligence engine (P108)/(P126)/(P136) is configured to record a plurality of indicators of the plurality of surgical lab instruments. The graphic user interface module (GUI) module (P103) communicatively connected to the authentication module (P106), the authentication module (P106) enables to authenticate a plurality of user credentials and detection of User RFID tags and/or bracelets to authenticate and record user id as per the activity of the plurality of users and the graphic user interface (GUI) module (P103) configured to represent a plurality of interactive user interactions for enabling a plurality of users to artificially relate to as a physical work space with a plurality of wizards to direct the plurality of users to login and perform an action.

In an embodiment, the artificial intelligence engine comprises the patient's module (P116) configured to automate control and track cassettes/equipment being applied to patients and enables end to end tracking with the plurality of surgical lab instruments to patient tracking.

In an embodiment, the artificial intelligence engine (P108)/(P126)/(P136) comprises the audit and reporting module (P118) configured to deal with a plurality of audit reports from the plurality of surgical lab instruments.

In an embodiment, the artificial intelligence engine (P108)/(P126)/(P136) comprises the training module (P120) configured to deal with context based training modules and reference manuals for the plurality of surgical lab instruments.

In an embodiment, the artificial intelligence engine (P108)/(P126)/(P136) comprises the inventory module (P122) configured to deal with requirement based auto replenishments of the plurality of surgical lab instruments.

In an embodiment, the artificial intelligence engine (P108)/(P126)/(P136) comprises the outsourced module (P124) configured to track inventory from the plurality of users, along with forward and reverse logistics.

In an embodiment, the artificial intelligence engine (P108)/(P126)/(P136) comprises at least one of: the content based artificial intelligence engine; the instrument recognition artificial intelligence engine; and the guidance providing artificial intelligence engine.

In an embodiment, the artificial intelligence engine (P108)/(P126)/(P136) is configured to facilitate the interaction between the plurality of surgical lab instruments.

In an embodiment, the plurality of surgical lab instruments comprises forceps, tongs, clamps, curettes, dental instruments, incubators, and combinations thereof.

In an embodiment, the patient tracking, audit and reporting module (P118) communicatively connected to the patient's module (P116) configured to provide a detailed audit report at the patient level.

In an embodiment, a method to monitor and track end to end sterilization reports using an automated sterilization system with artificial intelligence (AI) for processing surgical instruments, comprising: assigning and reading barcodes to a plurality of surgical lab instruments using the intelligent barcoding module (P110), identifying the plurality of surgical lab instruments assigned with barcodes by the artificial intelligence engine (P108)/(P126)/(P136) configured to communicatively coupled with the intelligent barcoding module (P110), the plurality of surgical lab instruments comprises at least one of: a sterilizer's module (P112) configured to automate, track and control sterilizer level test to ensure the plurality of surgical lab instruments are functioning as required, automating, tracking, and controlling the plurality of surgical lab instruments end to end sterilization workflow in coordination with the guidance provided by the artificial intelligence engine (P108)/(P126)/(P136), recording a plurality of indicators of the plurality of surgical lab instruments by the artificial intelligence engine (P108)/(P126)/(P136) and capturing communications between each of the modules and the users by the database (P128), the database (P128) comprises essentials for the artificial intelligence engine (P108)/(P126)/(P136) to perform actions using each module, enabling the authentication module (P106) to authenticate a plurality of user credentials and detecting a plurality of User RFID tags and/or bracelets and recording user id as per the activity of the plurality of users; and a graphic user interface (GUI) module (P103) communicatively connected to the authentication module (P106). The graphic user interface (GUI) module (P103) is configured to represent a plurality of interactive user interactions for enabling a plurality of users to artificially relate to as a physical work space with a plurality of wizards to direct the plurality of users to login and perform an action.

In an embodiment, the artificial intelligence engine (P108)/(P126)/(P136) performs an AI visual Scan to ensure the physical workspace operator is wearing a gear as per guidelines prescribed using criteria applicable for the plurality of users based on Geography, and practice type.

In an embodiment, the artificial intelligence engine (P108)/(P126)/(P136) performs an AI visual scan to ensure physical workspace setup is as per guidelines prescribed.

In an embodiment, the artificial intelligence engine (P108)/(P126)/(P136) comprises the Internet of things (IOT) indicator (P130b) indicates whether a plurality of indicators have reached the optimal limit intended for sterilization.

In an embodiment, the artificial intelligence engine (P108)/(P126)/(P136) recognizes the type of the plurality of surgical lab instruments.

In an embodiment, the artificial intelligence engine (P108)/(P126)/(P136) continuously updates the inventory of the plurality of surgical lab instruments utilized.

In an embodiment, the artificial intelligence engine (P108)/(P126)/(P136) automates, controls and tracks end to end flow using a SAAS platform.

In an embodiment, the artificial intelligence engine (P108)/(P126)/(P136) enhances tracking and controlling the Integration with the plurality of surgical lab instruments such as visibility of status, cycle runs and detailed reports, tracks the sterilization of plurality of surgical lab instruments all the way from sterilization cycle to patient used date and time stamp.

In an embodiment, the artificial intelligence engine (P108)/(P126)/(P136) automatically correlates a plurality of tests regarding the plurality of surgical lab instruments being used and the data collected automatically from the plurality of surgical lab instruments to avoid staff error or transcription error.

In an embodiment, a computer program product comprising a non-transitory computer-readable medium having a computer-readable program code embodied therein to be executed by one or more processors, said program code including instructions to: assign and read barcodes to a plurality of surgical lab instruments using the intelligent barcoding module (P110); identify the plurality of surgical lab instruments assigned with barcodes by the artificial intelligence engine (P108)/(P126)/(P136) configured to communicatively coupled with the intelligent barcoding module (P110), the plurality of surgical lab instruments comprises at least one of: a sterilizer's module (P112) configured to automate, track and control sterilizer level test to ensure the plurality of surgical lab instruments are functioning as required; automate, track, and control the plurality of surgical lab instruments end to end sterilization workflow in coordination with the guidance provided by the artificial intelligence engine (P108)/(P126)/(P136); record a plurality of indicators of the plurality of surgical lab instruments by the artificial intelligence engine (P108)/(P126)/(P136) and capturing communications between each of the modules and the users by the database (P128), the database (P128) comprises essentials for the artificial intelligence engine (P108)/(P126)/(P136) to perform actions using each module; enable the authentication module (P106) to authenticate a plurality of user credentials and detecting a plurality of User RFID tags and/or bracelets and recording user id as per the activity of the plurality of users; and the graphic user interface (GUI) module (P103) communicatively connected to the authentication module (P106), the graphic user interface (GUI) module (P103) configured to represent a plurality of interactive user interactions for enabling a plurality of users to artificially relate to as a physical work space with a plurality of wizards to direct the plurality of users to login and perform an action.

Figure 2:
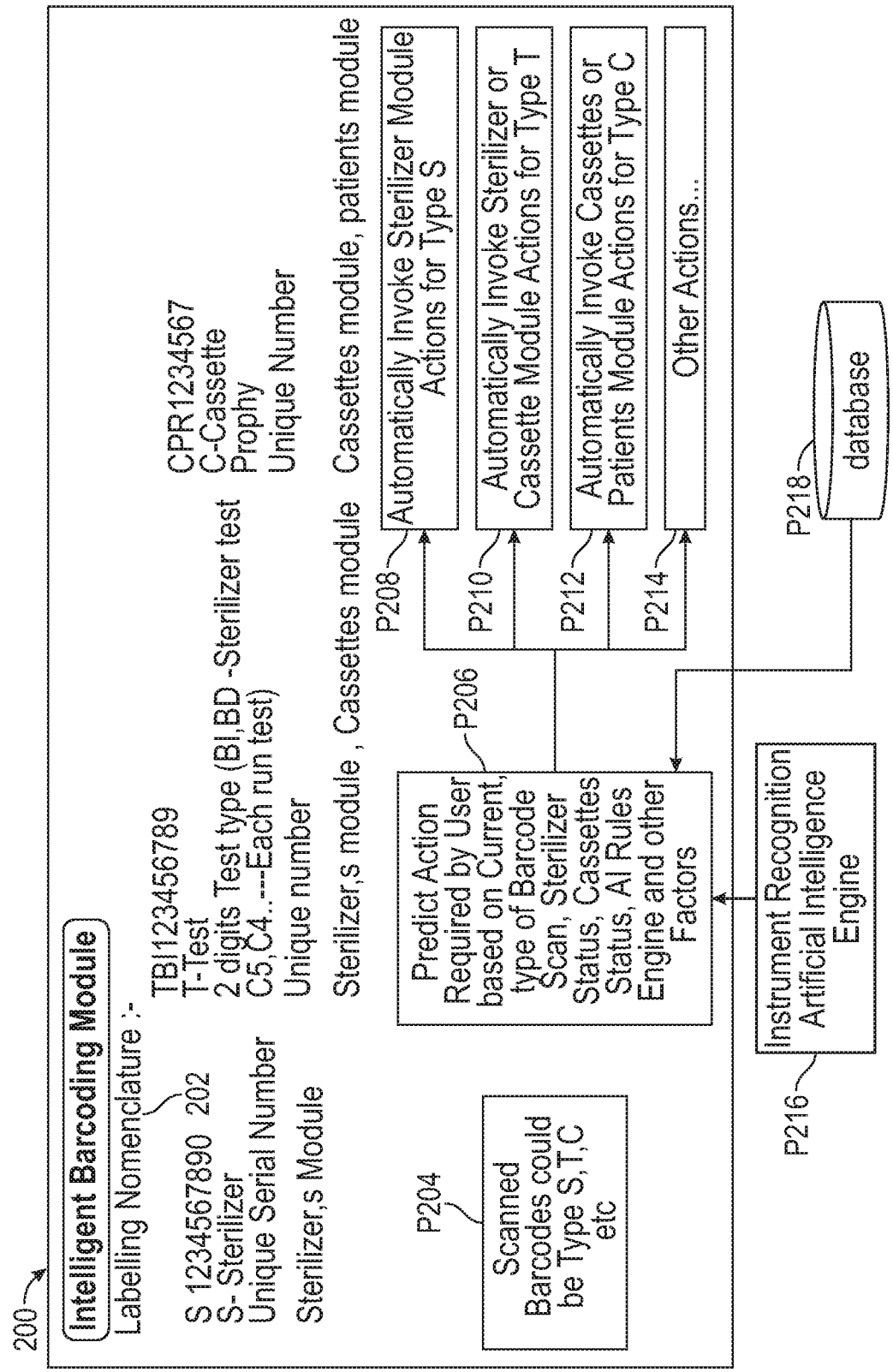
FIG. 2 is a block diagram an intelligent barcoding module, according to an embodiment of the present disclosure.

In accordance with a non-limiting exemplary embodiment of the present subject matter, FIG. 2 is a block diagram 200, depicting an intelligent barcoding module. Barcode may be defined as a machine readable data about the object which carries the barcode. As discussed in FIG. 1, the sterilizers, cassettes/pouches, instruments, physical indicators, to be sterilized are barcoded, not limiting to, Bowie Dick and/or biological indicator bar coded. The labelling nomenclature (P202) indicates various methods of interpreting the barcodes post scanning. The scanned barcodes (P204) may not be limited to, type S, type T, type C, and the like.

Example 1

S123456790
S—Sterilizer
Unique serial Number: 123456790
It perceives as interacted with the sterilizer module.

Example 2

TBI12345678
T—Test
2 digits Test type (BI, BD—Sterilizer test and C5,C4 . . . —Each run test)
Unique number: 123456789
It perceives as interacted with the sterilizer module and cassettes module.

Example 3

CPR1234567
C—Cassette
PR: Prophy
Unique Number: 1234567
It perceives as interacted with the cassettes module and patients module.

The system perception and analysis may be described as: Example 1 if the code starts with S, then the sterilizers module is invoked (P208), and similarly invoking the cassettes module or sterilizers' module actions for type T (P 210), or invoking cassettes or patient's module actions for type C (P212) and other actions (P214). The intelligent barcoding module with an instrument recognition artificial intelligence engine (P216) instrument set from the beginning of the Instrument Sterilization process all the way to the Patient. All BD, BI, other tests are automatically correlated to the instrument sets and sterilizers being used. The action required by the user is predicted based on; current type of Barcode scan, Sterilizer status, Cassettes status, AI Rules engine, and the like (P206). The interactions between each of the modules and the users and the end users are captured in the database (P218).

Figure 3:
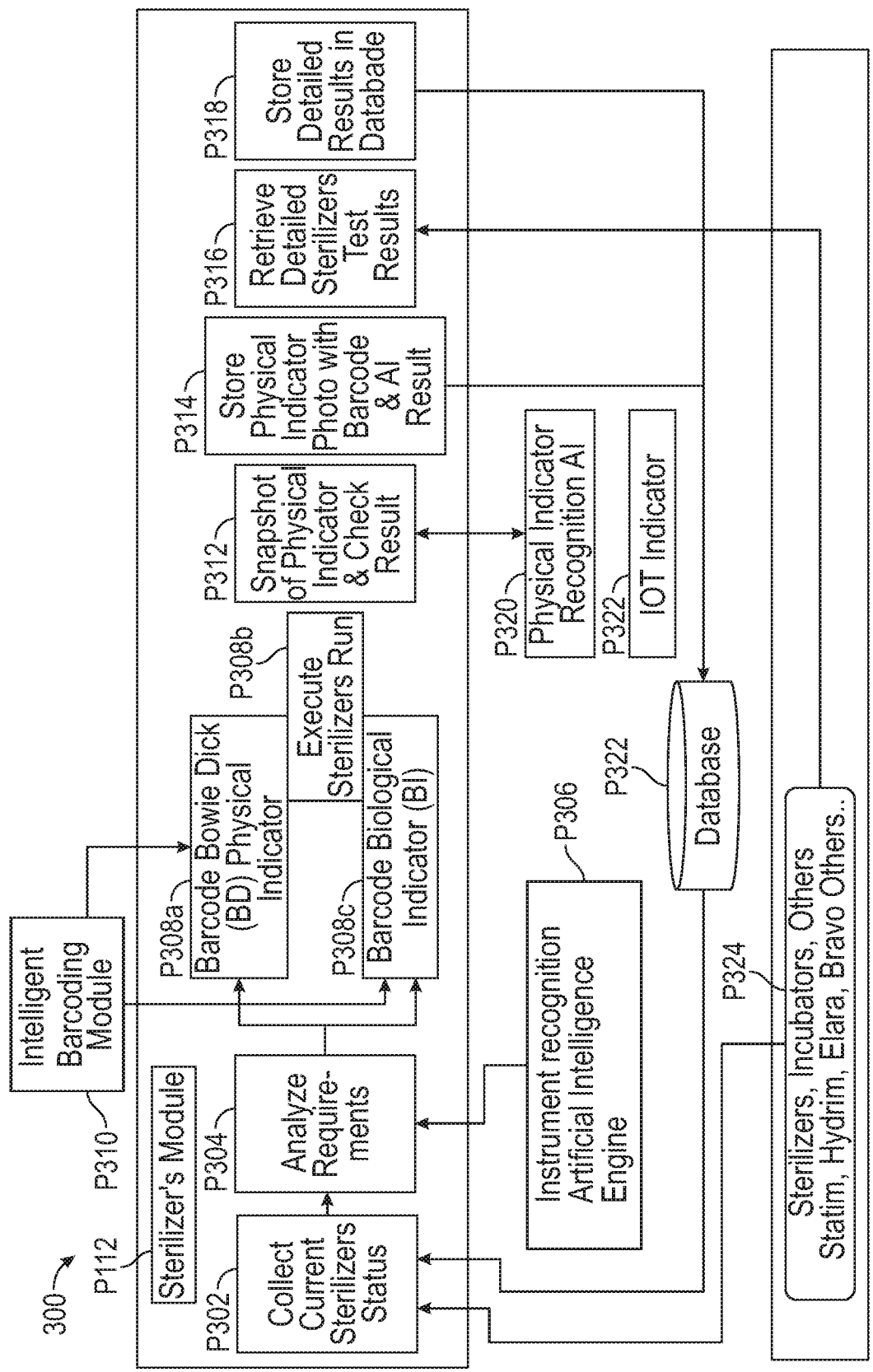
FIG. 3 is a block diagram depicting a sterilizer's module, according to an embodiment of the present disclosure.

According to a non-limiting exemplary embodiment of the present disclosure, FIG. 3 is a block diagram 300, depicting a sterilizer's module. The intelligent barcoding module (P310) as a function kicks in and checks if all the indicators are checked. The current status of the sterilizer, incubators, other instruments, and the like is checked (P302). These are machines in the lab (P324). The requirements are analyzed (P304) by instruments recognition artificial intelligence engine (P306) based on geography, practitioner, equipment, patient, and the like along with frequency of intervals at which the equipment for sterilization needs to be checked. Post analysis the barcode analysis is done based on physical indicators (P308a) via the physical indicators recognition AI (P320) and/or IOT indicator AI. The biological indicators (P308c) and execution of the running of the sterilizers (P308b). A snapshot of physical indicators and check results is obtained (P312). The physical indicator's photo with barcode and the result obtained by AI is stored (P314). The detailed sterilizers' test results are retrieved (P316), which is followed by storing of the test results (P318) in the database (P322).

Figure 4:
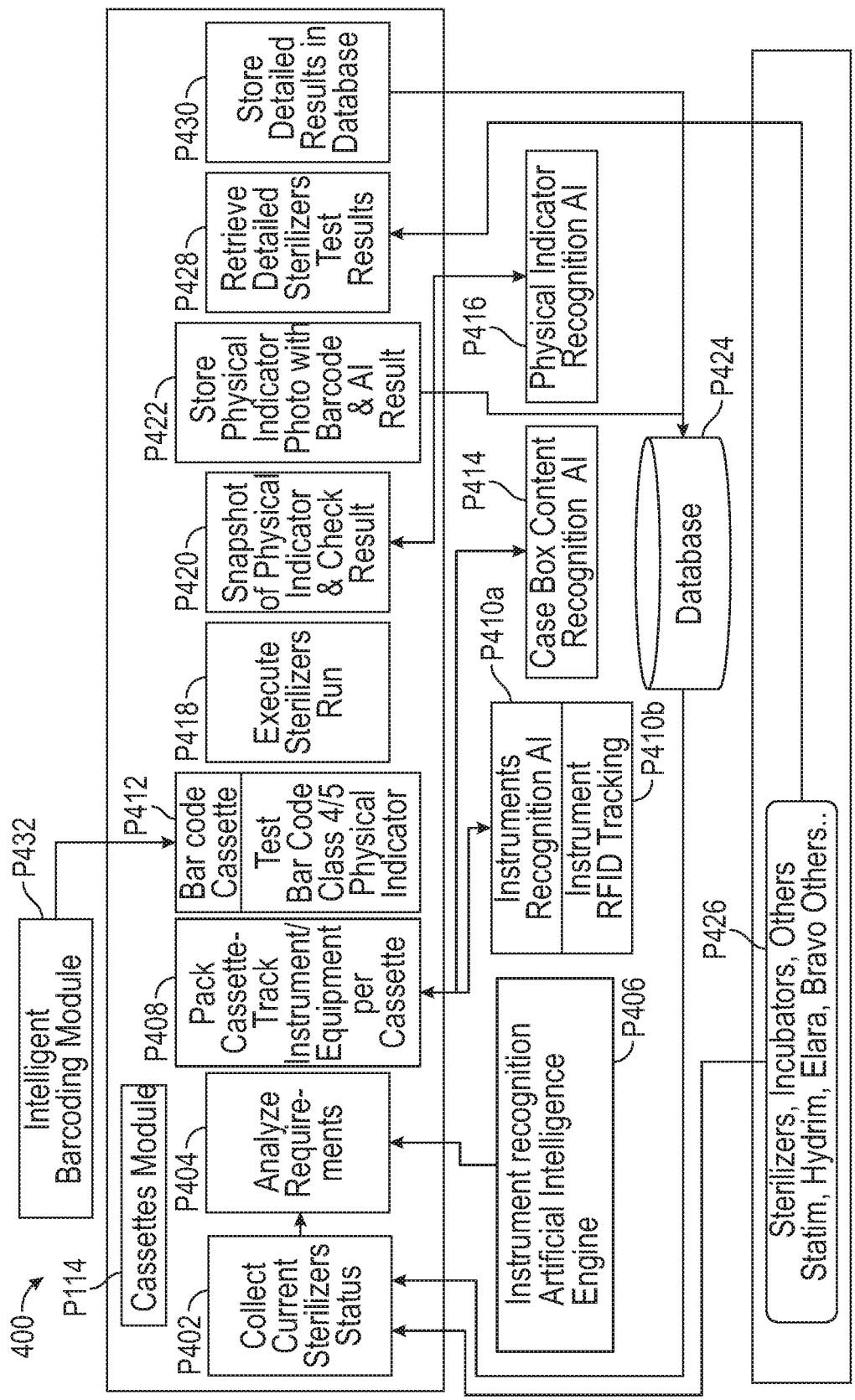
FIG. 4 is a block diagram depicting a cassette's module, according to an embodiment of the present disclosure.

In accordance with a non-limiting exemplary embodiment of the present subject matter, FIG. 4 is a block diagram 400, depicting a cassette's module. The cassettes module (P114) involves considering the current status (P402) of the sterilizers, incubators, and the like (P426). Cassettes are barcoded solutions which is unique to instruments undergoing sterilization. The cassettes are barcoded to go into sterilizers and the system. The requirements are analyzed (P404) by sterilization AI rules engine (P406) based on geography, practitioner, equipment, patient, and the like along with frequency of intervals at which the equipment for sterilization needs to be checked. Further, each instrument is packed in a cassette and each equipment is tracked as per the cassette (P408). The instruments recognition artificial intelligence engine (P410a) and Instruments RFID tracking engine (P410b) guide as to which kind of instrument is going into which kind of cassette. The case box content recognition AI (P414) is also involved in recognition of the case box. The intelligent barcoding module (P432) aids in reading cassettes with bar codes and testing the barcodes for analyzing the physical and biological indicators (P412). The running of sterilizers, incubators, and the like is executed (P418). The physical indicator recognition AI (P416) provides a snapshot of the physical indicators and the results are checked (P420). The pictographic format of the physical indicators and corresponding check results are stored (P422). The detailed form of the sterilizer's test results are retrieved (P428) and these detailed results are stored (P430) in the database (P424).

Figure 5:
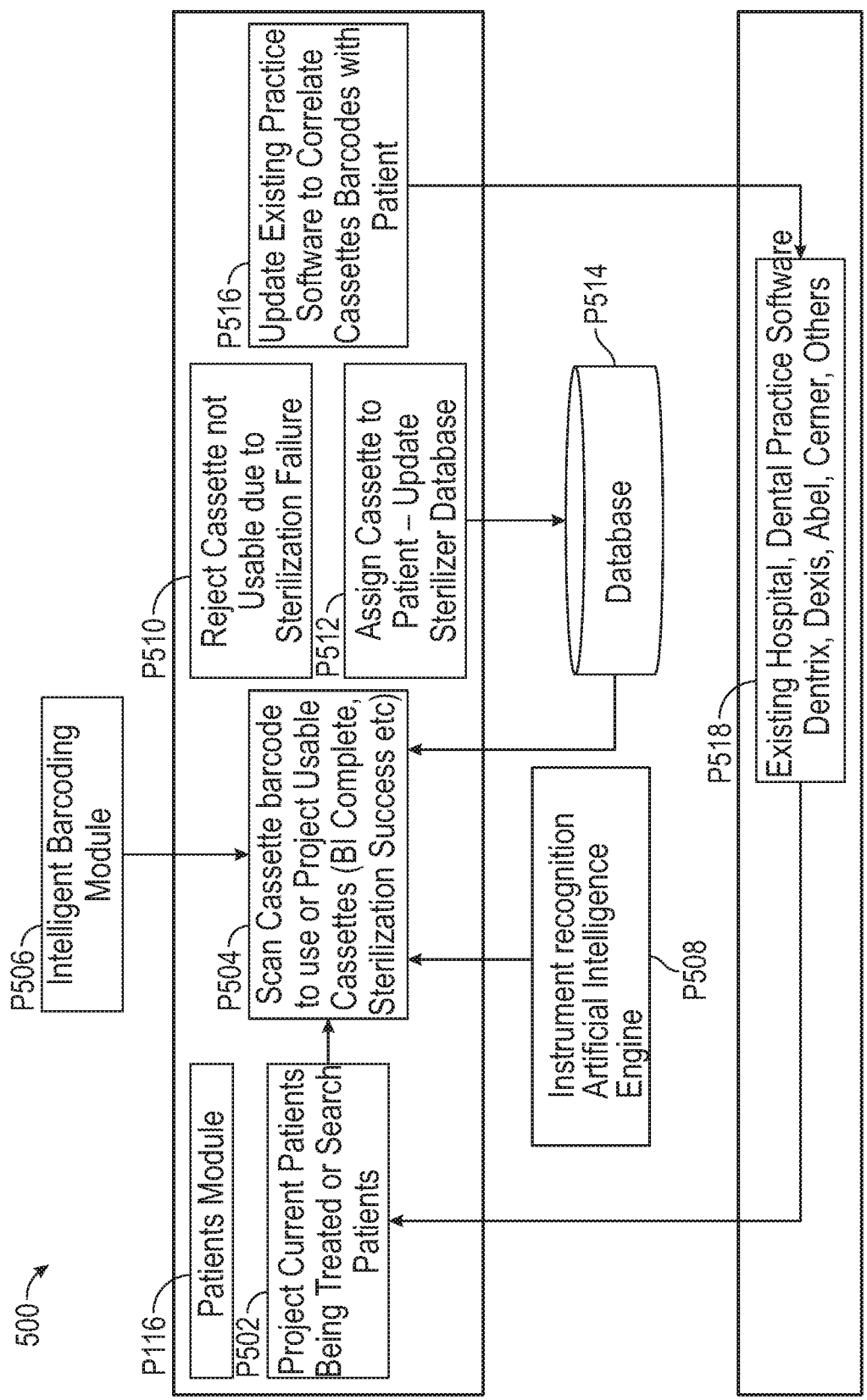
FIG. 5 is a block diagram depicting a patients module, according to an embodiment of the present disclosure.

According to a non-limiting exemplary embodiment of the present disclosure, FIG. 5 is a block diagram 500, depicting a patients' module. In the patients' module (P116), the existing hospitals, dental practice software, and the like (P518) project current trend of patients being treated and/or search the patients accordingly. The instruments recognition artificial intelligence engine (P508) based on geography, practitioner, equipment, patient, and the like scan the cassettes sterilization to use or to project the cassettes which are usable (P504) i.e. success of sterilization, and the like. Similarly, the intelligent barcoding module (P506) is used to test the already assigned barcodes to the cassettes. The instruments recognition artificial intelligence engine (P508) is used to project those cassettes which are not usable due to sterilization failure, and are rejected (P510). If the cassette is usable then, it is assigned to the patient and the database (P514) is updated as the process of step (P512). Finally, the existing practice software is updated to correlate cassettes barcodes with the patient (P516).

Figure 6:
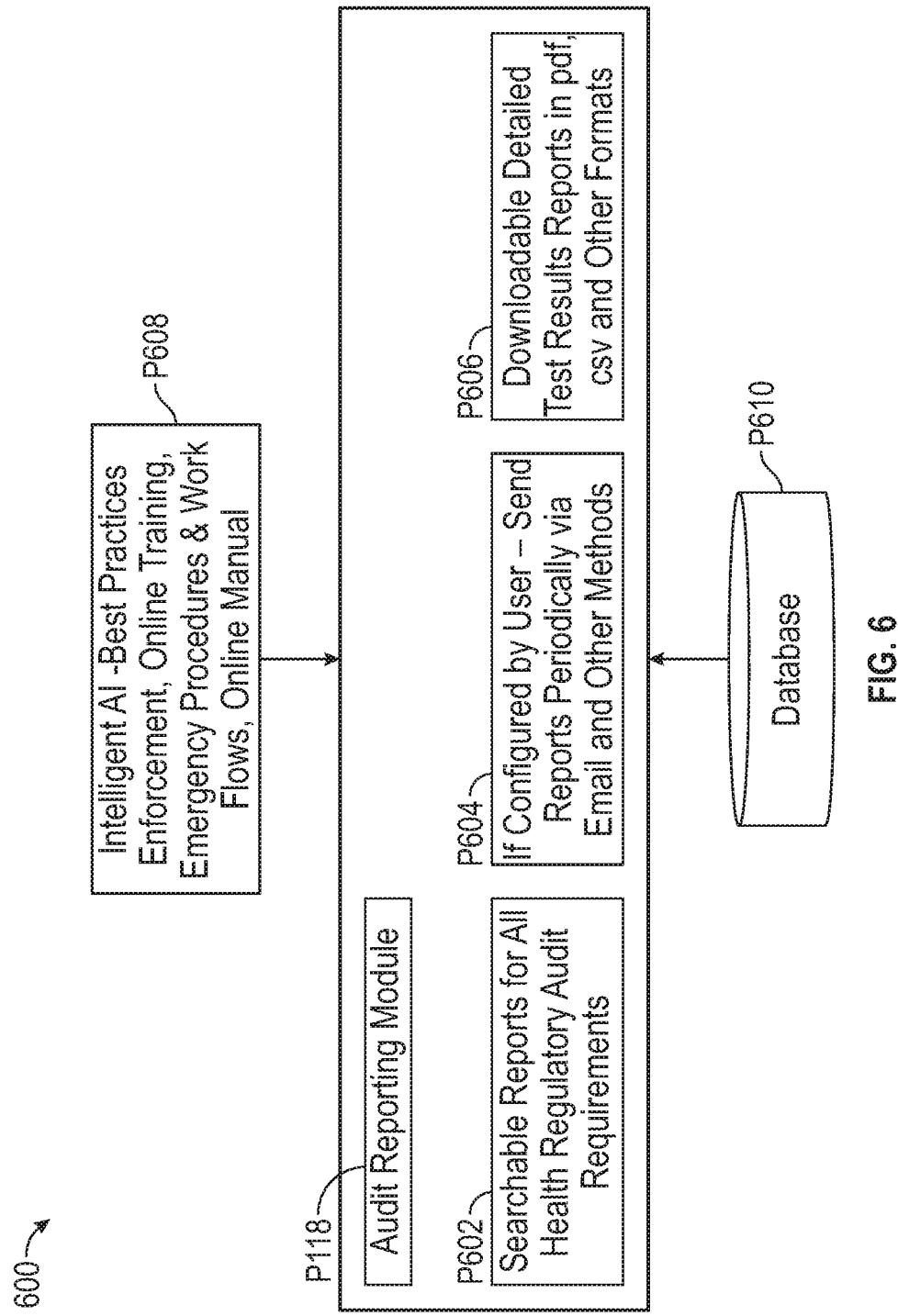
FIG. 6 is a block diagram depicting an audit and reporting module, according to an embodiment of the present disclosure.

In accordance with a non-limiting exemplary embodiment of the present subject matter, FIG. 6 is a block diagram 600, depicting an audit and reporting module, according to an embodiment of the present disclosure. The audit reporting module (P118) is the module which is accessible to the auditors and for the other users the flow of access to auditing information is blocked. The searchable reports for all the health regulatory audit requirements are obtained (P602). The reports are sent periodically via email and other methods when configured by the user (P604). The results stored in the database (P610) are downloadable in a detailed format as a PDF, CSV, and the like (P606). All the reporting is derived from the database (P610). The process of audit reporting module utilized the AI engine for best practice enforcement, online training, emergency procedures, and online workflow manual.

Figure 7:
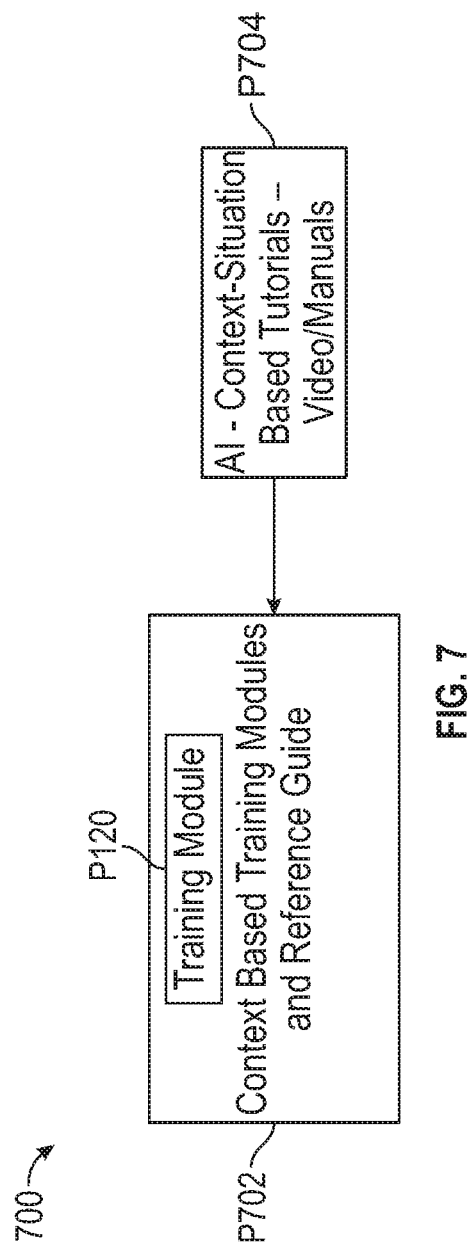
FIG. 7 is a block diagram depicting a training module, according to an embodiment of the present disclosure.

According to a non-limiting exemplary embodiment of the present disclosure, FIG. 7 is a block diagram 700, depicting a training module. The training module (P 120) includes context based training modules and reference guide for the user (P702) which is directed by the AI based on context, situation tutorials in the form of a video and/or a written manual available as, not limiting to, a soft copy. The location of the manual virtually is depicted in FIG. 9 subsequently.

Figure 8:
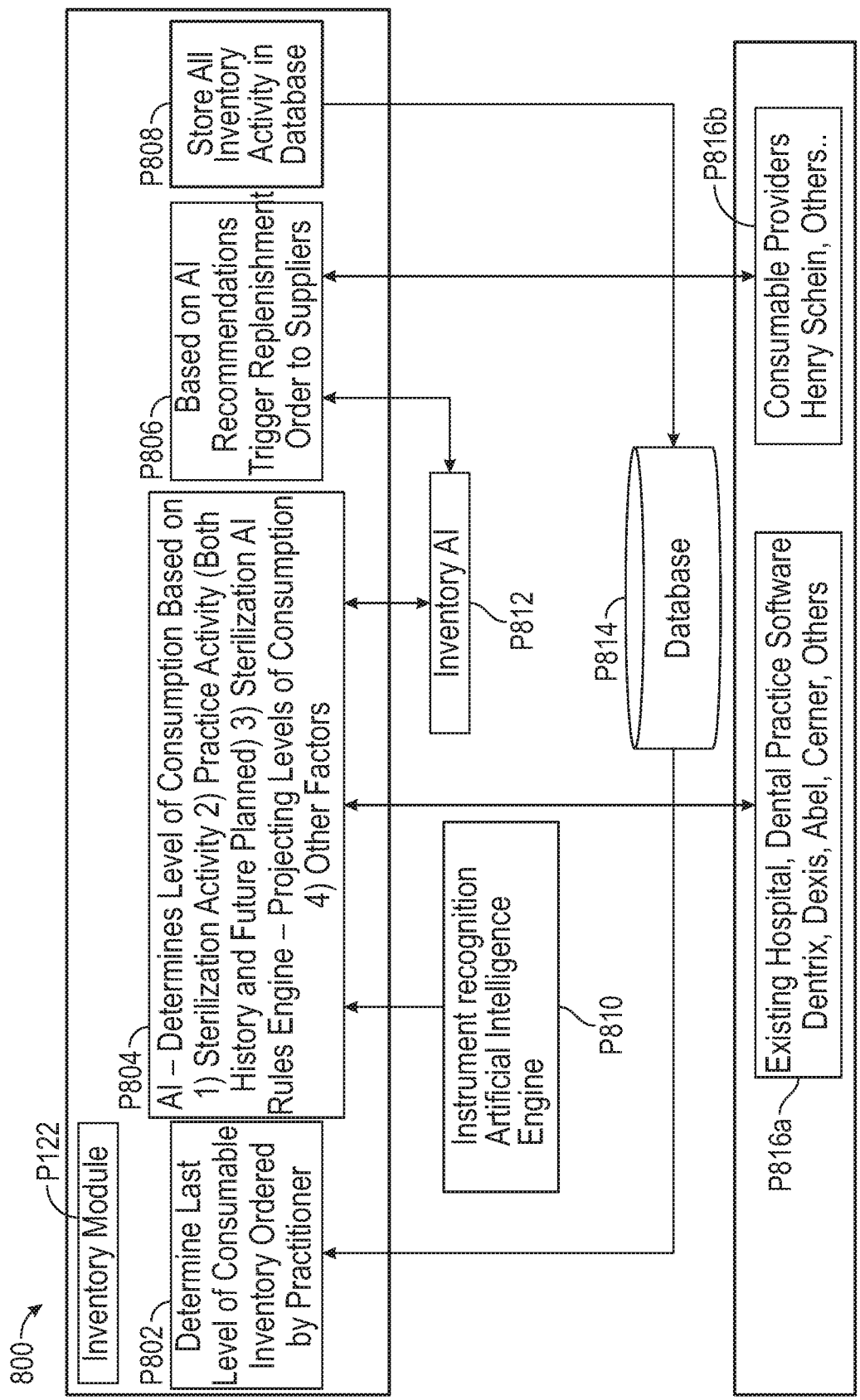
FIG. 8 is a block diagram depicting an inventory module, according to an embodiment of the present disclosure.

In accordance with a non-limiting exemplary embodiment of the present subject matter, FIG. 8 is a block diagram 800, depicting an inventory module. In the inventory module (P122) the last level of consumable inventory ordered by the practitioner is determined (P802). The sterilization AI rules engine (P814) which is based on geography, practitioner, equipment, patient, and the like determines level of consumption based on: sterilization activity; Practice activity (both history and future planned); Sterilization AI rules engine—projecting levels of consumption; and other factors (P804) and instrument recognition artificial intelligence module P810. This consumption level determination is derived from existing hospitals, dental practices software, and the like (P816a). The inventory AI (P812) is also linked to (P804). Based in on the recommendations of (P812) replenishment order to suppliers is triggered (P806), where the consumable provides (P816b) supply the requisite materials, not limiting to, BD discards, pouches, and the like. The records of the entire inventory (P808) are stored in the database (P814). The amount of patient activity which has taken place is recorded by the artificial intelligence module.

Figure 9:
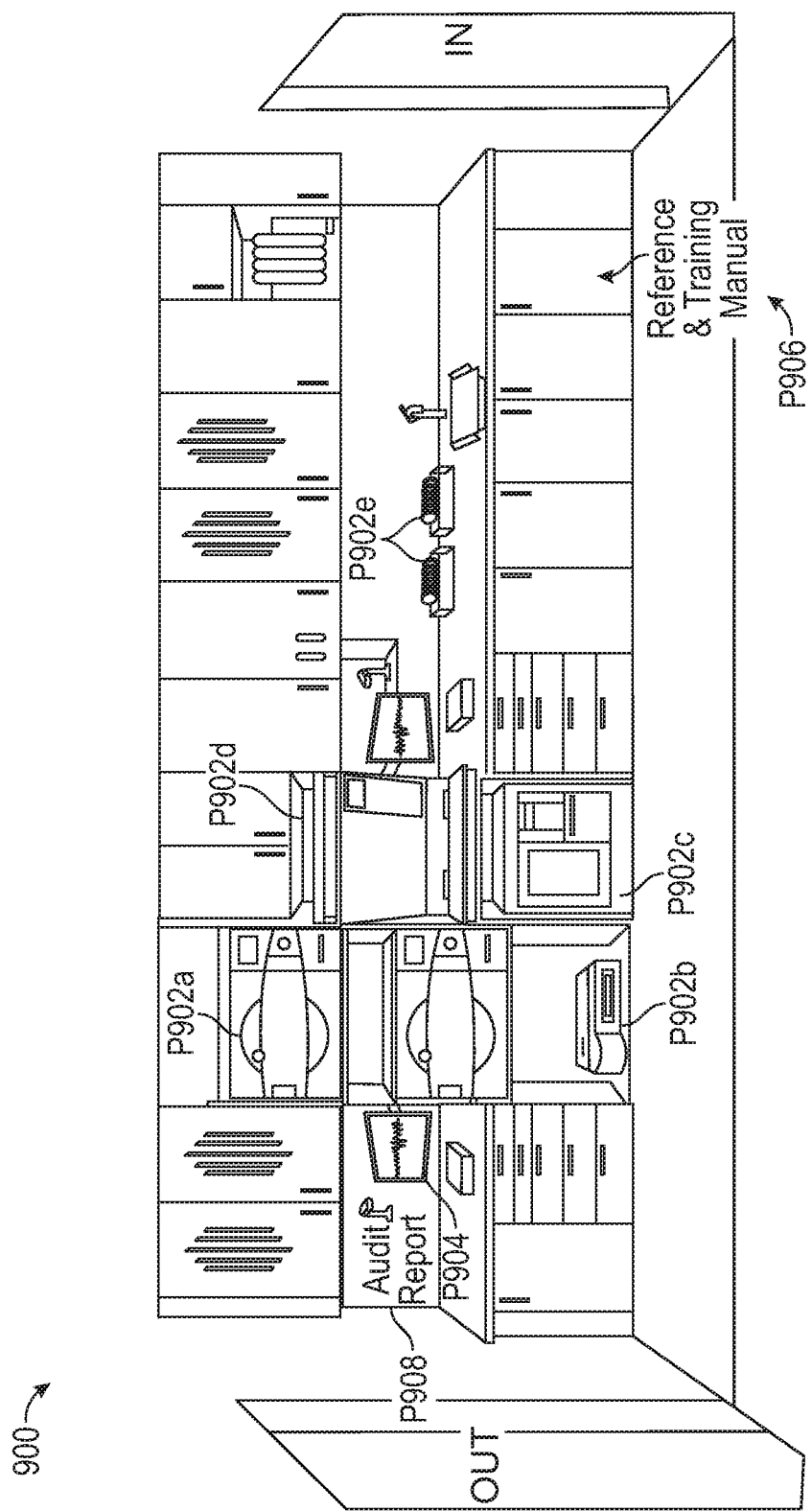
FIG. 9 is a schematic representation of an interactive; Wizards enabled GUI pictorial representation of the physical workspace of the practitioner, according to an embodiment of the present disclosure.

According to a non-limiting exemplary embodiment of the present disclosure, FIG. 9 is a schematic representation 900, of the interactive GUI depicting the physical space of the practices sterilization area. The various pictures, icons are clickable to perform corresponding actions. Various data is displayed on the GUI similar to what a user will see on the physical sterilizers and surrounding areas. Example cycle number, status etc. are displayed on the sterilizer picture with pending action buttons of ease of use for the user. The interactive intelligent GUI only displays action buttons that the user is allowed to perform—the wizards & workflow guide the user to the next steps to be performed. In the FIG. 900, the various equipment used in the sterilization process is depicted from (P902a-P902e). The equipment may not be limited to, sterilizers, incubators, cassettes, pouches, autoclaves, barcodes, indicator tapes, and the like. The cycle number and status of the equipment are depicted as an example in (P902a and P902d). Cycle number is fed and the user can scan the process through the user's device. The system keeps two unique ID's: the Sterilizer serial number and the cycle number. Physical indicators are not limiting to, temperature, pressure, or time required for the cycle to be operated in order for the instruments to be sterilized. An instruction to update the load (P902c) is depicted. The "IN" and "OUT" depict the inlet of the sterilization GUI menu similar to the user walking in and out of the areaPost "IN" lies the access to reference and training manual (P906)—which will execute the training module with the online manual and training videos/materials upon selection. Selecting any of the sterilizers (P902a, P902D etc.) will launch the relevant functions of the Sterilizer module. Similarly cassettes (P902e) placed on the counter top will launch the relevant cassettes modules functions. The audit report option is displayed (P908) will launch the audit reporting module functions. The report may be accessed by clicking on the option. The screen (P904) when selected will launch the patient module which will allow the user to assign cassettes to patients.

Figure 10:
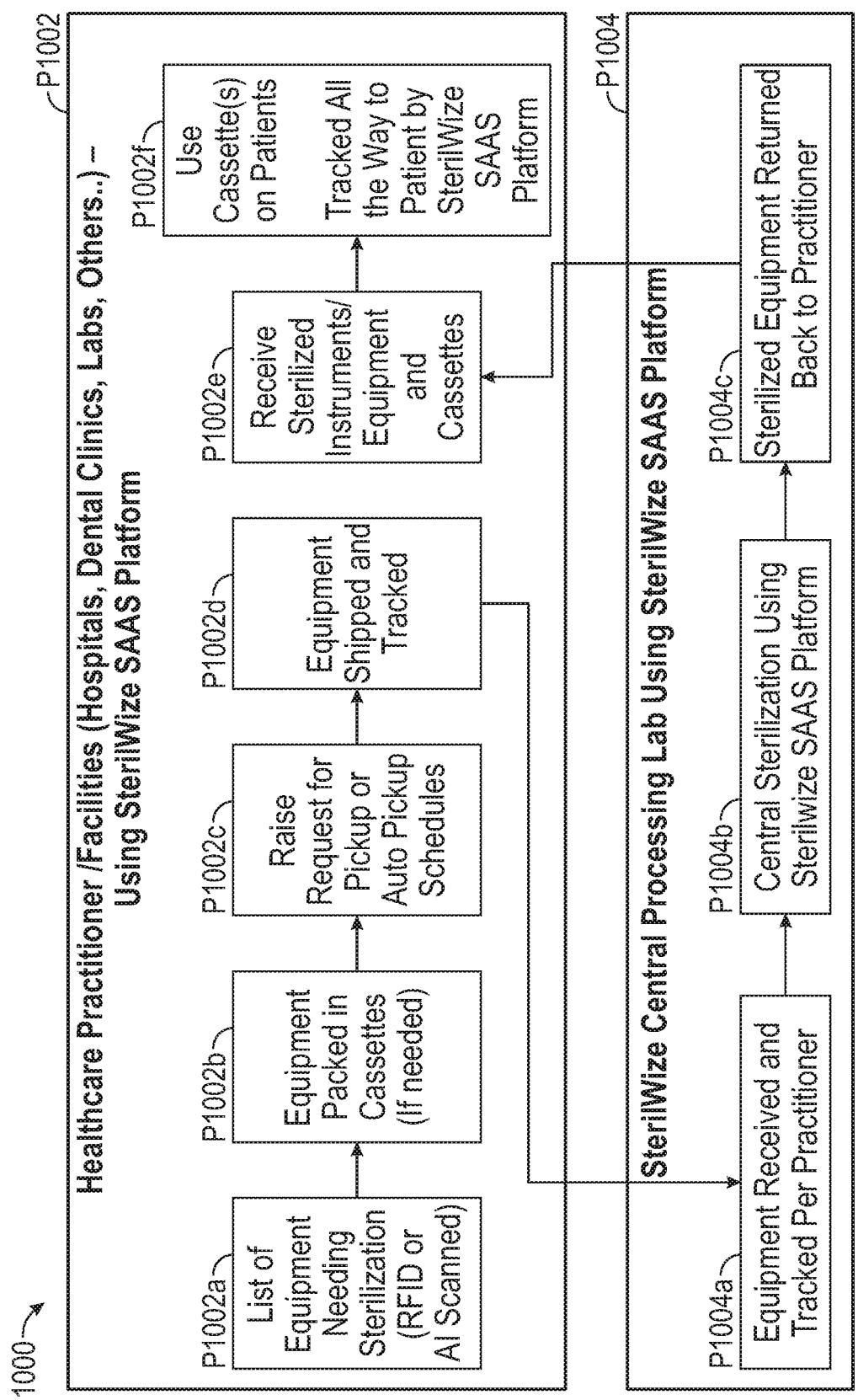
FIG. 10 is a physical activity model diagram depicting an outsourcing platform, according to an embodiment of the present disclosure.

In accordance with a non-limiting exemplary embodiment of the present subject matter, FIG. 10 is a block diagram 1000, depicting an outsourcing model whereby the practitioner wants to outsource all sterilization activities. Practitioner identifies the equipment to be sterilized which is picked by SterilWize central processing team or the designated logistics provider. Sterilization is performed at the central SterilWize location and returned to the practitioner. Subsequently the practitioner assigns the clean cassettes to its patients. The end to end flow is automated, controlled and tracked using the SterilWize SAAS platform. The activity takes place through a cloud computing platform SAAS (P1002) which is utilized by the healthcare facilities which intend to outsource sterilization of its instruments. The figure depicts the collaboration between (P1002) and central processing lab (P1004) [depicted as sterilwize central processing lab, using sterilwize SAAS platform]. In the platform (P1002) the equipment which need sterilization are tracked by RFID or AI scanned are listed (P1002a). The equipment is packed in cassettes (P1002b). The request to pick or auto pick up schedules is raised (P1002c). The equipment which is shipped is tracked (P1002d) and further the sterilized equipment and/instruments and corresponding cassettes are received (P1002e). The AI engine which facilitates the interaction is the instrument recognition AI and the cassette recognition AI. The used cassettes on patients are tracked all the way to the patient through the SAAS platform (P1002f). Likewise, in the central processing lab (P1004) the tracked equipment of (P1002d) is received and tracked per practitioner (P1004a) which is further directed to the central sterilization unit using SAAS platform (P1004b), and the sterilized equipment is returned to the practitioner (P1004e). As another embodiment the equipment may be provided by the sterilization lab itself to the practitioners.

Figure 11:
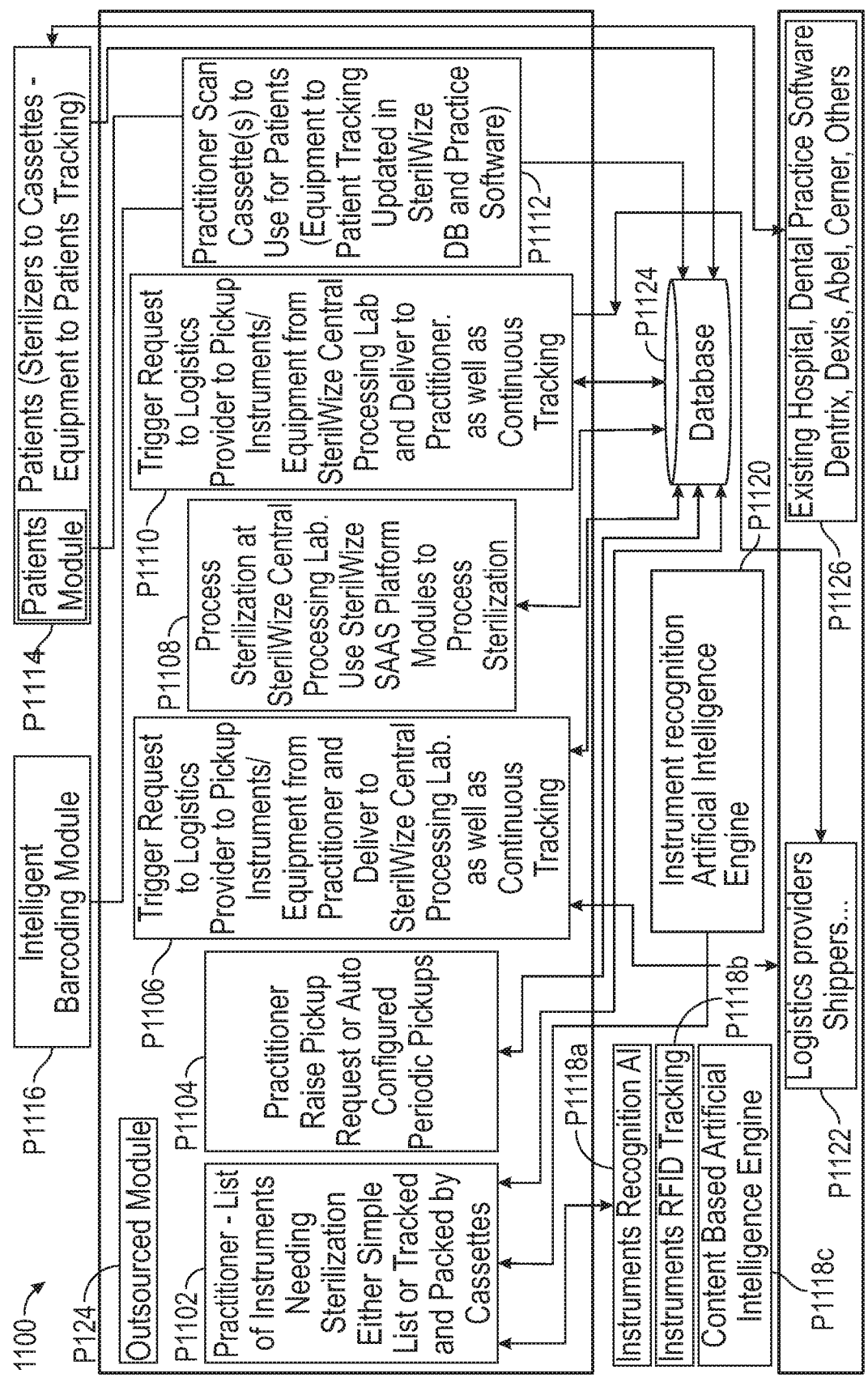
FIG. 11 is a system interaction diagram depicting an outsourcing module, according to an embodiment of the present disclosure.

According to a non-limiting exemplary embodiment of the present disclosure, FIG. 11 is a block diagram 1100, depicting the systems interaction corresponding to the outsourcing module explained above. In the outsourced module (P124), Instruments recognition AI, instruments RFID Tracking engine, and case box content recognition engine (P1118a), (P1118b), and P (1118c) respectively, along with instruments recognition artificial intelligence engine based on geography, practitioner, equipment, patient and other factors, collaborate to aid the practitioner in figuring out the list of instruments needing sterilization, which may not be limited to, a simple list, or those tracked and packed by cassettes (P1102). Practitioner raises the pickup request and/or auto configures periodic pickups (P1104). Further, requests is triggered to a logistics provider to pickup instruments and/or equipment from practitioner and deliver to Central processing lab and perform continuous tracking as well (P1106). The logistic providers (P1122) are connected to (P1106). Further, processing sterilization at the central processing lab by using SAAS platform modules is performed (P1108). Further, a request is triggered to the logistics provider to pick up instruments and/or equipment from central processing lab and delivering it to practitioner and perform continuous tracking as well (P1110). It is for the next stage where the patients module (P1114) kicks in along with an interaction with the existing hospitals, and dental practice software (P1126). The intelligent barcoding module (P1116) helps the practitioner to scan the cassette(s) to use for patients (P1112), where the equipment to patient tracking updated in database (P1124) and practice software.

Figure 12:
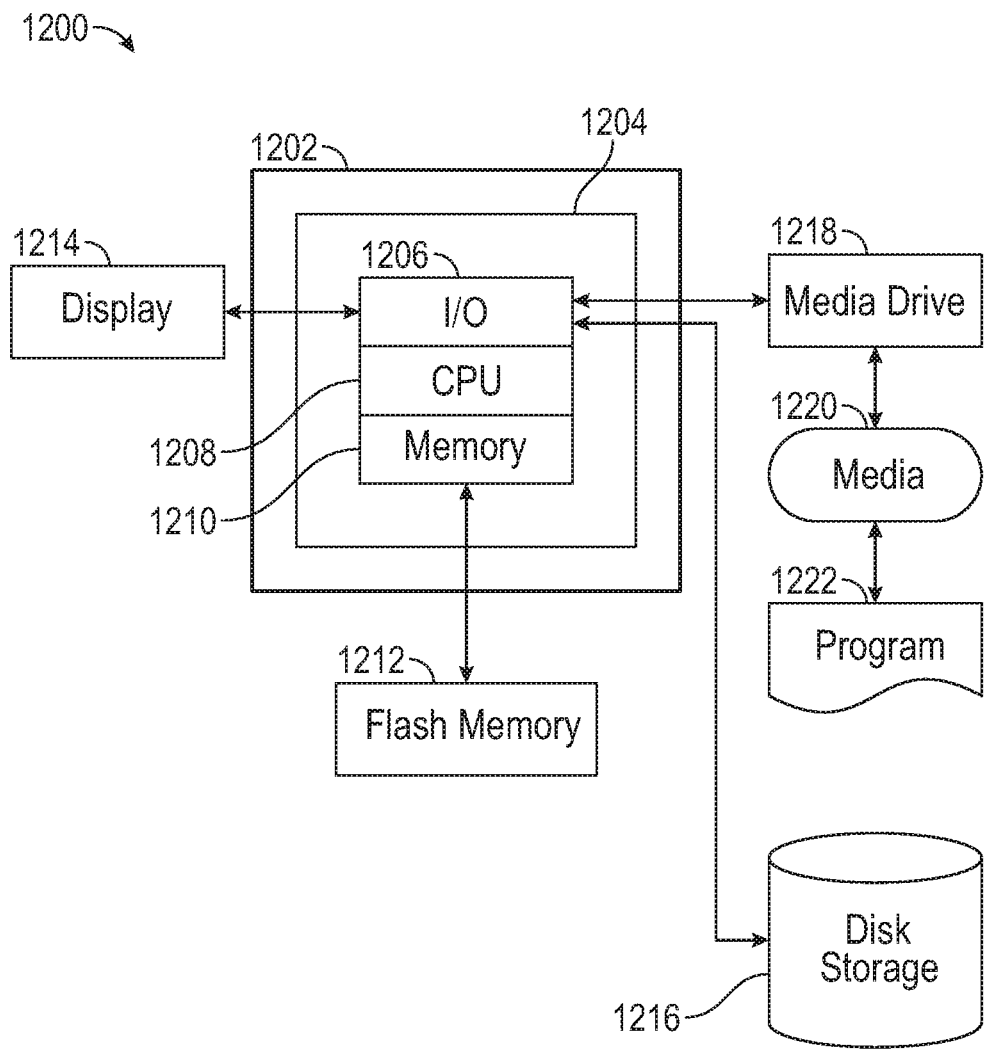
FIG. 12 is a block diagram illustrating the details of processing system in which various aspects of the present disclosure are operative by execution of appropriate instructions.

Referring to FIG. 12 is a block diagram of a computing system 1200, illustrating the details of the processing system in which various aspects of the present disclosure are operative by execution of appropriate instructions. FIG. 12 depicts an exemplary computing system 1200 that can be configured to perform any one of the processes provided herein. In this context, computing system 1200 may include, for example, a processor, memory, storage, and I/O devices (e.g., monitor, keyboard, disk drive, Internet connection, etc.). However, computing system 1200 may include circuitry or other specialized hardware for carrying out some or all aspects of the processes. In some operational settings, computing system 1200 may be configured as a system that includes one or more units, each of which is configured to carry out some aspects of the processes either in software, hardware, or some combination thereof.

FIG. 12 depicts computing system 1200 with a number of components that may be used to perform any of the processes described herein. The main system 1202 includes a motherboard 1204 having an I/O section 1206, one or more central processing units (CPU) 1208, and a memory section 1210, which may have a flash memory card 1212 related to it. The I/O section 1206 can be connected to a display 1214, a keyboard and/or other user input (not shown), a disk storage unit 1216, and a media drive unit 1218. The media drive unit 1218 can read/write a computer-readable medium 1220, which can contain programs 1222 and/or data. Computing system 1200 can include a web browser. Moreover, it is noted that computing system 1200 can be configured to include additional systems in order to fulfill various functionalities. Computing system 1200 can communicate with other computing devices based on various computer communication protocols such a Wi-Fi, Bluetooth® (and/or other standards for exchanging data over short distances includes those using short-wavelength radio transmissions), USB, Ethernet, cellular, an ultrasonic local area communication protocol, etc.

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub combinations of the various features described herein above as well as variations and modifications thereof, which would occur to persons skilled in the art upon reading the foregoing description.

We claim:

1. An automated sterilization system with artificial intelligence (AI) for processing surgical instruments, comprising:
a plurality of surgical lab instruments comprises at least one of: a sterilizer's module configured to automate, track and control sterilizer level test to ensure the plurality of surgical lab instruments are functioning as required using physical indicator tests such as Bowie dick (BD) tests, Biological Indicator (BI) tests, and other physical indicators in coordination with the guidance provided by an artificial intelligence engine; a cassettes module configured to automate, track and control cassettes/pouches end to end sterilization workflow in coordination with the guidance provided by the artificial intelligence engine; the artificial intelligence engine configured to perform all processes, tasks, workflows, AI visual Scans as per guidelines prescribed using criteria applicable for a plurality of users based on Geography, practice type, Equipments being used, type of procedures, patients;
the artificial intelligence engine configured to record a plurality of indicators of the plurality of surgical lab instruments, the artificial intelligence engine comprises an Internet of things (IOT) indicator indicates whether a plurality of indicators have reached an optimal limit intended for sterilization, the artificial intelligence engine (AI) analyzes physical indicators automatically to determine pass or fail conditions; and
a graphic user interface module (GUI) module communicatively connected to an authentication module, whereby the authentication module configured to authenticate a plurality of user credentials and detection of User RFID tags and/or bracelets to authenticate and record user id as per the activity of the plurality of users and the graphic user interface module (GUI) module configured to represent a plurality of interactive user interactions for enabling the plurality of users to artificially relate to as a physical work space with a plurality of wizards to direct the plurality of users to login and perform an action.

2. Wherein the artificial intelligence engine comprises a patient's module configured to automate workflow produce a plurality of audit reports and track cassettes/equipment being applied to patients and enables end to end tracking with the plurality of surgical lab instruments to patient tracking.

3. The system of claim 1, wherein the artificial intelligence engine comprises an audit and reporting module configured to deal with a plurality of end-to-end audit reports from the plurality of sterilization procedures, cassettes to equipment to the patient level, physical indicators, sterilizers data, incubators, surgical lab instruments and any other data required by local regulations, the artificial intelligence engine determines the level of reporting required based on local regulatory requirements, geography, type of practitioner, type of sterilization equipment and procedures as well as other factor.

4. The artificial intelligence engine comprises a best practices enforcement, workflows, training module configured to deal with context based training modules and reference guide for the user which is directed by the artificial intelligence based on context, context situation based tutorials, videos and reference manuals for the plurality of various sterilization procedures or the plurality of surgical lab instruments.

5. The system of claim 1, wherein the artificial intelligence engine comprises an inventory module configured to deal with requirements based auto replenishments of the plurality of sterilization lab consumables, the various consumable inventory is monitored and depreciated based on various factors such as types and amounts of sterilization cycles executed, the auto replenishment of consumable inventories triggers are sent to suppliers automatically by artificial intelligence demand predictions based on usage trends, geography and other factors.

6. The system of claim 1, wherein the artificial intelligence engine comprises at least one of: a content based artificial intelligence engine; an instrument recognition artificial intelligence engine; case box/cassette content recognition artificial intelligence engine and a guidance providing artificial intelligence engine configured to identify results of the sterilization of the plurality of surgical lab instruments placed in the cassettes/pouches.

7. The system of claim 1, wherein the artificial intelligence engine configured to facilitate the interaction between the plurality of sterilization procedures, workflows, rules, patients, surgical lab instruments by identifying a stage of sterilization, identifying the results and then guide the plurality of users for the plurality of various sterilization procedures.

8. The system of claim 1, wherein the patient tracking, audit and reporting module communicatively connected to the patient's module configured to provide a detailed audit report from sterilizers, incubators, cassettes, equipment, users, detailed action timelines, and sterilization area machines to the patient level.

9. A method to monitor and track end to end sterilization reports using an automated sterilization system with artificial intelligence (AI) for processing surgical instruments, comprising:
a plurality of surgical lab instruments comprises at least one of: a sterilizer's module configured to automate, track and control sterilizer level test to ensure the plurality of surgical lab instruments are functioning as required using physical indicator tests such as Bowie Dick (BD) tests, Biological Indicator (BI) tests, and other physical indicators in coordination with a guidance provided by an artificial intelligence engine;
automating, tracking, and controlling the plurality of surgical lab instruments end to end sterilization workflow in coordination with the guidance provided by the artificial intelligence engine; the artificial intelligence engine configured to perform all processes, tasks, workflows, AI visual Scans as per guidelines prescribed using criteria applicable for a plurality of users based on Geography, practice type, Equipments being used, type of procedures, patients;
recording a plurality of indicators of the plurality of surgical lab instruments by the artificial intelligence engine, the artificial intelligence engine comprises an Internet of things (IOT) indicator indicates whether a plurality of indicators have reached an optimal limit intended for sterilization, the artificial intelligence engine (AI) analyzes Physical indicators automatically to determine pass or fail conditions;
enabling an authentication module to authenticate a plurality of user credentials and detecting a plurality of User RFID tags and/or bracelets and recording user id as per the activity of the plurality of users; and a graphic user interface module (GUI) module communicatively connected to the authentication module, whereby the graphic user interface module (GUI) module configured to represent a plurality of interactive user interactions for enabling the plurality of users to artificially relate to as a physical work space with a plurality of wizards to direct the plurality of users to login and perform an action.

10. The method of claim 9, wherein the artificial intelligence engine performs an artificial intelligence visual scan to ensure physical workspace setup is as per guidelines prescribed and also to ensure a sterilization lab operator is wearing a protective gear as per guidelines prescribed by the best practices artificial intelligence (AI) engine using criteria applicable for the practitioner based on Geography, local regulations and practice type.

11. The method of claim 9, wherein the artificial intelligence engine ensures the number of instruments going into surgery/treatment are returned to sterilization areas in totality, the artificial intelligence engine recognizes and documents the list and the types of the plurality of instruments being checked out of sterilization area as well as the plurality of instruments in a case box/cassette/pouch based on image artificial intelligence or RFID or barcodes, on return of the plurality of instruments post-surgery/treatment, the artificial intelligence engine automatically ensures the plurality of instruments have been returned to the Sterilization area.

12. The method of claim 9, wherein the artificial intelligence engine continuously updates an inventory of the plurality of surgical lab instruments utilized, a surgical lab instruments inventory is kept track based on where the instruments are physically located as well as number of sterilizations it has gone through, the artificial intelligence engine generates alerts for replenishment of the plurality of surgical lab instruments based on guidelines of wear and tear.

13. The method of claim 9, wherein the artificial intelligence engine automates, controls and tracks end to end flow using a cloud computing platform.

14. The method of claim 9, wherein the artificial intelligence engine enhances tracking and controlling the Integration with the plurality of surgical lab instruments such as visibility of status, cycle runs and detailed reports, tracks the sterilization of plurality of surgical lab instruments, the artificial intelligence engine comprises the history of cycle numbers with sterilizers, records results of all the tests run on the sterilizers.

15. The method of claim 9, wherein the artificial intelligence engine automatically correlates a plurality of tests regarding end to end sterilization workflow of a plurality of sterilizers, incubators, washers, hydrims, other machines, surgical lab equipment being used and the data collected automatically from the plurality of surgical lab equipment to avoid staff error or transcription error.

16. A method for providing outsourced sterilization services comprising of:
functionality providing outsourced sterilization services whereby practitioners (Dental clinics, medical clinics, hospitals, universities and others) outsource all sterilization activities;
an artificial intelligence engine comprises an outsourced module which allows for the process of outsourcing of all Sterilization activities, whereby the outsourced module is configured to track an inventory between an outsourced sterilization centre, practitioners, logistics providers and a plurality of users along with forward and reverse logistics;
packing unsterilized equipment in cassettes at a practitioner site by scanning equipment based on RFID or intelligent barcoding using instruments recognition artificial intelligence engine configured to guide as to which kind of equipment is going into which kind of cassette;
raising request for pickup or auto pickup from the practitioner of the unsterilized equipment by a logistics provider;
tracking and receiving the unsterilized equipment by the outsourced sterilization centre;
processing end to end sterilization workflow at the outsourced sterilization centre;
packing sterilized equipment in cassettes at the outsourced sterilization centre by scanning equipment based on RFID or intelligent barcoding or using an instrument recognition artificial intelligence engine configured to guide as to which kind of equipment is going into which kind of cassette;
raising request for pickup or auto pickup from the outsourced sterilization centre of sterilized equipment by the logistics provider;
tracking and receiving sterilized equipment by the practitioner;
tracking usage and inventory of sterilized as well as the unsterilized equipment at the practitioner site; and
triggering auto pickup of unsterilized equipment from the practitioner site.

17. A computer program product comprising a non-transitory computer-readable medium having a computer-readable program code embodied therein to be executed by one or more processors, said program code including instructions to:
a plurality of surgical lab instruments comprises at least one of: a sterilizer's module configured to automate, track and control sterilizer level test to ensure the plurality of surgical lab instruments are functioning as required using physical indicator tests such as Bowie Dick (BD) tests, Biological Indicator (BI) tests, and other physical indicators in coordination with a guidance provided by an artificial intelligence engine;
automate, track, and control the plurality of surgical lab instruments end to end sterilization workflow in coordination with the guidance provided by the artificial intelligence engine; the artificial intelligence engine configured to perform all processes, tasks, workflows, AI visual Scans as per guidelines prescribed using criteria applicable for a plurality of users based on Geography, practice type, Equipments being used, type of procedures, patients;
record a plurality of indicators of the plurality of surgical lab instruments by the artificial intelligence engine the artificial intelligence engine comprises an Internet of things (IOT) indicator (P130*b*) indicates whether a plurality of indicators have reached an optimal limit intended for sterilization, the artificial intelligence engine (AI) analyzes physical indicators automatically to determine pass or fail conditions;
enable an authentication module to authenticate a plurality of user credentials and detecting a plurality of User RFID tags and/or bracelets and recording user id as per the activity of the plurality of users; and
a graphic user interface module (GUI) module communicatively connected to the authentication module, whereby the graphic user interface module (GUI) module configured to represent a plurality of interactive user interactions for enabling a plurality of users to artificially relate to as a physical work space with a plurality of wizards to direct the plurality of users to login and perform an action.

* * * * *